United States Patent
Aoki

(10) Patent No.: US 6,821,527 B2
(45) Date of Patent: Nov. 23, 2004

(54) SYSTEM FOR TREATING KIDNEY DISEASE IN DIABETIC AND NON-DIABETIC PATIENTS

(76) Inventor: Thomas T. Aoki, 1021 El Sur Way, Sacramento, CA (US) 95825

(*) Notice: Subject to any disclaimer, the term of this patent is extended or adjusted under 35 U.S.C. 154(b) by 68 days.

(21) Appl. No.: 10/393,424

(22) Filed: Mar. 19, 2003

(65) Prior Publication Data

US 2003/0176323 A1 Sep. 18, 2003

Related U.S. Application Data

(62) Division of application No. 09/881,826, filed on Jun. 15, 2001, now Pat. No. 6,613,342.
(60) Provisional application No. 60/212,132, filed on Jun. 16, 2000.

(51) Int. Cl.[7] .............................. A61F 2/02; A61K 9/08
(52) U.S. Cl. ........................ 424/422; 424/400; 424/423
(58) Field of Search ............................... 424/400, 422, 424/423

(56) References Cited

U.S. PATENT DOCUMENTS 5,100,392 A * 3/1992 Orth et al. .................. 604/175
6,613,342 B2 * 9/2003 Aoki .......................... 424/422

* cited by examiner

Primary Examiner—Carlos A. Azpuru
(74) Attorney, Agent, or Firm—Eric G. Masamori

(57) ABSTRACT

The present invention is a system capable of improving the entire metabolic process and through its multiplicity of effects on neurovascular reactivity, intraglomerular pressure and hemodynamics, arresting the progression of overt diabetic nephropathy, improving intraglomerular hemodynamics, and thus arresting the progression of diabetic nephropathy and therefore reducing the risk of development of End Stage Renal Disease. The current system is for the treatment of kidney disease using insulin pulses to a patient utilizing Chronic Intermittent Intravenous Insulin Therapy to achieve the slowing, stopping or reversing of kidney disease in both diabetic and non-diabetic patients.

4 Claims, No Drawings

SYSTEM FOR TREATING KIDNEY DISEASE IN DIABETIC AND NON-DIABETIC PATIENTS

CROSS REFERENCE TO OTHER APPLICATIONS

This application is a divisional of Ser. No. 09/881,826, filed Jun. 15, 2001, now U.S. Pat. No. 6,613,342 which claims benefit of provisional application 60/212132, filed Jun. 16, 2000.

FIELD OF INVENTION

This invention relates to the treatment of kidney disease in diabetic and non-diabetic patients. More specifically, the invention relates to a system for treating kidney disease in diabetic and non-diabetic patients with Chronic Intermittent Intravenous Insulin Therapy.

BACKGROUND OF THE INVENTION

Diabetic kidney disease (nephropathy) develops in 35 to 40% of patients with type 1 diabetes mellitus (DM) and in 10 to 60% of patients with type 2 DM depending upon the ethnic pool being studied. It is the most common cause of End-Stage Renal Disease (ESRD) in the United States. Experts generally have assumed that diabetic nephropathy is the result of hyperglycemia, whether alone or in combination with other factors, such as hypertension and genetic susceptibility to kidney disease. Two major recent clinical trials involving patients with type 1 DM (Diabetes Control and Complication Trial [DCCT]) and type 2 DM (United Kingdom Prospective Diabetes Study [UKPDS]) have demonstrated that improved glycemic control reduces the onset and the progression of early diabetic nephropathy to overt nephropathy in patients recently diagnosed with diabetes mellitus (DM) thereby giving additional credence to the hypothesis that a lack of glycemic control is the primary cause. Both of theses studies used recently diagnosed patients some of whom, although well controlled, went on to develop kidney disease. Since the DCCT and UKPDS studies demonstrated that near normalization of blood glucose level did not always result in a delay of the onset or progression of diabetic nephropathy, the hypothesis that euglycemia is the means for addressing this disease, is made suspect.

Once nephropathy has become clinically overt (that is, macroalbuminuria and decreased glomerular filtration rate are detected), the degree of glycemic control is shown to have lost its importance as a factor. This observation provides additional evidence to refute the claim that glycemic control is the primary factor to be addressed in kidney disease, and that other mechanisms have greater overall influence. Indeed, most patients with DM and proteinuria eventually will progress to ESRD or premature death from cardiovascular complications. In such patients, with no medical intervention, the glomerular filtration rate decreases an average of 1 ml/min per month, a deterioration that leads to ESRD in a mean period of 7 years. Once overt persistent proteinuria is established, no known strategy exists that can stop or reverse the progression to ESRD. Appropriate antihypertensive therapy has been shown to significantly reduce renal and possibly cardiovascular mortality in proteinuric type 1 DM patients, as well as retard the rate of decline of glomerular filtration rate in some patients with impaired renal function (Lewis A J et al, N Engl J Med 1993, 329:1456–62). Thus, the standard of care for patients with diabetic nephropathy is intensive glycemic control and normalization of the blood pressure using primarily angiotensin converting enzyme inhibitors.

The pathophysiology of diabetic nephropathy is only partially understood. The most consistent morphologic finding in diabetic nephropathy is the enlargement of the mesangium, which can compress the glomerular capillaries and thus alter intraglomerular hemodynamics. McLennan et al (Diabetes, 1994,43:1041–45) showed that a high glucose concentration inhibits degradation of the mesangium and could promote the mesangial enlargement observed in diabetic nephropathy.

The inventor hypothesizes that an improvement in the entire metabolic milieu as observed with Chronic Intermittent Intravenous Insulin Therapy (CIIIT) could reverse the process discussed above and have favorable effects on the progression of overt diabetic nephropathy. Furthermore, Chronic Intermittent Intravenous Insulin Therapy has been shown to improve blood pressure control substantially and to reduce by 46% the antihypertensive medication requirements in patients with type 1 DM (Aoki T T et al, Diabetes Care, 1995,18:1260–65), possibly through an improvement in vascular reactivity. This effect was hypothesized by the inventor to favorably influence the intraglomerular hemodynamics and delay the progression of diabetes-related renal disease.

What is needed is a system that improves the entire metabolic process and through its multiplicity of effects on neurovascular reactivity, intraglomerular pressure and hemodynamics, could arrest the progression of overt diabetic nephropathy, improve intraglomerular hemodynamics, and thus arrest the progression of diabetic nephropathy and therefore reduce the risk of development of ESRD.

SUMMARY

Accordingly, the present invention is a system capable of improving the entire metabolic process and through its multiplicity of effects on neurovascular reactivity, intraglomerular pressure and hemodynamics, arresting the progression of overt diabetic nephropathy, improving intraglomerular hemodynamics, and thus arresting the progression of diabetic nephropathy and therefore reducing the risk of development of ESRD. The current invention is the treating of kidney disease using insulin pulses to a patient utilizing Chronic Intermittent Intravenous Insulin Therapy to achieve the slowing, stopping or reversing of kidney disease in both diabetic and non-diabetic patients.

One preferred embodiment of the invention is a system for treating kidney disease in diabetic and non-diabetic patients through an intravenous administration of a pulse of insulin comprises a means for determining a respiratory quotient of a patient, a liquid or food containing glucose, an intravenous site, and a means of delivering a pulse of insulin at a regular interval of time.

In the preferred embodiment of the treatment system, any instrument capable of measuring the respiratory quotient determines a respiratory quotient of a patient. The respiratory quotient is defined as the ratio of carbon dioxide produced to oxygen consumed by the patient. In the preferred embodiment, a liquid or food containing glucose is consumed by the patient to prevent hypoglycemia. The preferred liquid or food containing glucose is GLUCOLA, however any similar liquid or food containing glucose that will prevent hypoglycemia in the patient may be used.

The preferred means of delivering insulin is an infusion device. It is preferable that the infusion device is capable of providing pulses of insulin on a prearranged interval, so long as there is sufficient glucose in the blood to keep the patient from becoming hypoglycemic. The preferred infusion device is also capable of delivering the pulses of insulin in as short duration of time as possible, without adversely affecting the vein at the site of infusion is used. However, less accurate devices may deliver the pulses and achieve the needed infusion profile.

In the preferred embodiment, the intravenous site is a temporary or permanent IV access site located in the body, forearm or hand of the patient. The amount of insulin is tailored to achieve more normal metabolic function of the kidney. Metabolic function is measured as stabilization or decrease in 24-hour urinary protein excretion or stabilization or increase in creatinine clearance. Type 1 diabetic patients receive 20–35 milliunits of insulin per kilogram of body weight per pulse and type 2 diabetic patients receive 70–200 milliunits of insulin per kilogram of body weight per pulse. During periods of non-use, the IV site is preferably converted to a heparin or saline lock.

In one embodiment of the method of the invention, the patient is seated in a blood drawing chair and a 23 gauge needle/catheter is inserted into a hand or forearm vein to obtain vascular access. Although a 23 gauge needle catheter is preferred, any system of such access may accomplish the needed result, including indwelling catheters. After a short equilibration period, usually thirty minutes, the respiratory quotient (the ratio of carbon dioxide produced to oxygen consumed by the patient) of the patient is measured. The respiratory quotient measuring device may be any presently known model manufactured by any presently known supplier of such instruments. In the preferred embodiment, the patient is then asked to drink or eat liquid or food containing glucose usually on the order of 60 to 100 grams of glucose. In the preferred embodiment a pulse of insulin is administered intravenously on a regular interval of time, usually every six minutes, until the respiratory quotient (RQ) shows improvement, as indicated by a respiratory quotient of 0.90 or greater. In the preferred embodiment, improvement in RQ is generally achieved within one hour. In the preferred embodiment, the insulin/oral glucose phase is then followed by a rest period of usually one hour. In the preferred embodiment the entire procedure repeated until the desired effect is achieved.

The preferred method of insulin pulse delivery would be a prearranged interval, so long as there is sufficient glucose in the blood to keep the patient from becoming hypoglycemic. In order to determine the progress of the patient, it is preferable the RQ is measured every hour and blood glucose levels are checked every 30 minutes. The blood glucose level may be measured by any means which shows that the patient is not becoming hypoglycemic. In the preferred embodiment, the patient is free to move around after the initial insulin pulses have been administered. In the preferred embodiment, the intravenous site is converted to a heparin or saline lock. The patient returns to the blood drawing chair to receive their next series of insulin pulses. In the preferred embodiment, the subsequent insulin pulses must be covered by supplying glucose by mouth or other means. The total time of the preferred procedure is approximately 6–7 hours.

In the preferred embodiment, two successive days of three treatments are performed with a new patient. In the preferred embodiment, the above is repeated once a week. For patients who need a more intensive approach, it is preferable the procedure be repeated 3 or more times, including continuously each week until the desired clinical outcome is achieved.

In the non-diabetic patient more glucose may be required than in the diabetic patient, but the other parameters would remain the same, including the need for a pulse delivery.

DETAILED DESCRIPTION OF THE INVENTION

The following description is provided to enable any person skilled in the art to use the invention and sets forth the best mode presently contemplated by the inventor of carrying out his invention. Various modifications, however, will remain readily apparent to those skilled in the art, as generic principles of the present invention have been defined herein.

The present invention is a system capable of improving the entire metabolic process and through its multiplicity of effects on neurovascular reactivity, intraglomerular pressure and hemodynamics, arresting the progression of overt diabetic nephropathy, improving intraglomerular hemodynamics, and thus arresting the progression of diabetic nephropathy and therefore reducing the risk of development of ESRD. The current invention is a system and method of treating of kidney disease using insulin pulses to a patient utilizing a Chronic Intermittent Intravenous Insulin Therapy to achieve the slowing, stopping or reversing of kidney disease in both diabetic and non-diabetic patients.

The preferred embodiment of the invention is a system and method of delivering insulin pulses to a patient utilizing a Chronic Intermittent Intravenous Insulin Therapy. The preferred embodiment of the treatment system comprises a means for determining a respiratory quotient of a patient, a liquid or food containing glucose, an intravenous site, and a means of delivering a pulse of insulin at a regular interval of time.

The preferred means for determining a respiratory quotient of a patient is a SENSORMEDIC METABOLIC MEASUREMENT CART, however any instrument capable of measuring the respiratory quotient may be used. The respiratory quotient is defined as the ratio of carbon dioxide produced to oxygen consumed by the patient.

The liquid or food containing glucose is consumed by the patient to prevent the patient from becoming hypoglycemic. The preferred liquid or food containing glucose is GLUCOLA, but any similar type of liquid or food containing glucose may be given to the patient.

The preferred means of insulin delivery would be an infusion device capable of providing pulses of insulin on a prearranged interval, so long as there is sufficient glucose in the blood to keep the patient from becoming hypoglycemic. It is also preferable that the infusion device is capable of delivering the pulses of insulin in as short duration of time as possible, without adversely affecting the vein at the site of infusion is used. The preferred infusion device is the BIONICA MD-110. However, less accurate devices may deliver the pulses and achieve the needed infusion profile.

In the preferred embodiment, a temporary or permanent intravenous access site located in the body, forearm or hand of the patient, whereby insulin is provided by intravenous pulses in a highly accurate manner, however any type of similar temporary or permanent intravenous access may be used. Currently, a 23 gauge catheter is inserted in to a hand or forearm vein. The amount of insulin is tailored to achieve more normal metabolic function of the kidney. The metabolic function is measured by stabilization or decrease in 24-hour urinary protein excretion or stabilization or increase in creatinine clearance. Type 1 diabetic patients receive 20–35 milliunits of insulin per kilogram of body weight per pulse and type 2 diabetic patients receive 70–200 milliunits of insulin per kilogram of body weight per pulse. During periods of non-use, the intravenous site is preferably converted to a heparin or saline lock.

The preferred embodiment of the method of delivering insulin pulses to a patient utilizing Chronic Intermittent Intravenous Insulin Therapy is as follows. On the morning of the procedure, the patient is preferably seated in a blood drawing chair and a 23 gauge needle or catheter is preferably inserted into a hand or forearm vein to obtain vascular access. However, any system of such access may accomplish the needed result, including indwelling catheters, PICC lines and PORTACATHs. After a short equilibration period the patient is asked to breathe into an instrument which measures the patient's respiratory quotient. Equilibrium is achieved when consecutive measurements of the respiratory quotient, at least 5 minutes apart, are the same and are less than 0.90. In practice the equilibration period was thirty minutes, however any period of time that allows patient to establish a steady baseline, may be used. It is preferable that a SENSORMEDIC METABOLIC MEASUREMENT CART is used to measure the respiratory quotient, however, any presently known model manufactured by any presently known supplier of instruments capable of measuring a respiratory quotient may be used.

After the RQ is obtained, the patient is asked to consume a liquid or food containing glucose. The amount of glucose given to the patient ranged from 60 to 100 grams, however the amount of initial glucose given to the patient may vary. A pulse of insulin is then administered intravenously on a regular interval of time until the measured RQ shows improvement, as indicated by a RQ of 0.90 or greater. The usual interval of time was every six minutes, however, other regular intervals of time may be used. Improvement in RQ is generally achieved within one hour, however, the time required for RQ improvement may be shorter or longer than one hour.

The insulin/glucose phase is followed by a rest period of usually one hour. The rest period allows the elevated insulin levels to return to baseline. The entire procedure is repeated until the desired effect, RQ greater than 0.90, is achieved. The preferred method of insulin delivery would be providing pulses of insulin on a prearranged interval, so long as there is sufficient glucose in the blood to keep the patient from becoming hypoglycemic. In order to determine the progress of the patient, the RQ is measured every hour and blood glucose levels are checked every thirty minutes by any means which shows that the patient is not becoming hypoglycemic.

Once the insulin pulses have been administered and the patient shows RQ improvement as indicated by a RQ of 0.90 or greater, the patient is provided a rest period. During the rest period the patient is allowed to move around until the next series of insulin pulses are administered. During the rest period the IV site is preferably converted to a heparin or saline lock. The total time of the procedure is approximately 6–7 hours.

The amount of insulin is tailored to achieve more normal metabolic function of the kidney. The stabilization or decrease in 24-hour urinary protein excretion or the stabilization or increase in creatinine clearance measures metabolic function of the kidney. Type 1 diabetic patients receive 20–35 milliunits of insulin per kilogram of body weight per pulse and type 2 diabetic patients receive 70–200 milliunits of insulin per kilogram of body weight per pulse.

Usually with a new patient two successive days of three treatments are performed the first week. For continuing patients the procedure is performed once a week. For patients who need/require a more intensive approach, the procedure may be repeated 3 or more times, including continuously, each week until the desired clinical outcome is achieved. The intensive approach is designed for patients whose 24-hour urinary protein excretion is unchanged or increases or whose creatinine clearance continues to fall. The desired clinical outcome is a decrease in urinary protein excretion in a 24-hour period or the stabilization of the fall or increase in creatinine clearance.

In the non-diabetic patient more glucose may be required than in the diabetic patient, but the other parameters would remain the same, including the need for pulse delivery.

The following non-limiting example is given by way of illustration only.

EXAMPLE 1

The inventor hypothesized that the Chronic Intermittent Intravenous Insulin Therapy (CIIIT) procedure, through its multiplicity of effects on neurovascular reactivity, intraglomerular pressure, and hemodynamics, may arrest the progression of overt diabetic nephropathy, improve intraglomerular hemodynamics, and thus arrest the progression of diabetic nephropathy and therefore reduce the risk of development of ESRD.

These results have been confirmed in a multi-center, long-term (37 months) retrospective longitudinal study of 31 patients with type 1 DM (Aoki T T et al, Endocrine Practice, 1999, 5:174–78). This study indicated that CIIIT seems to arrest or appreciably reduce the progression of overt diabetic nephropathy. Creatinine clearance remained essentially unchanged [from 46.1±3.0 ml/min at baseline to 46.0±3.9 ml/min at the end of the observation period], and substantial improvement in the glycemic control (hemoglobin A1c levels declined from 8.6±0.6 to 7.6±0.3% [P=0.0062] during the study period) in patients with type 1 DM and diabetic nephropathy was found.

The preferred embodiments described herein are illustrative only, and although the examples given include many specificity's, they are intended as illustrative of only a few possible embodiments of the invention. Other embodiments and modifications will, no doubt, occur to those skilled in the art. The examples given should only be interpreted as illustrations of some of the preferred embodiments of the invention, and the full scope of the invention should be determined by the appended claims and their legal equivalents.

What is claimed is:

1. A system for treating kidney disease in diabetic and non-diabetic patients through an intravenous site administering a pulse of insulin to a patient comprising:

a) a means for determining a steady baseline respiratory quotient of the patient and obtaining a subsequent respiratory quotient every 30 minutes, the steady baseline respiratory quotient being two identical consecutive respiratory quotients less than 0.90 measured five minutes apart, b) a liquid or food containing 60 to 100 grams of glucose, the liquid or food containing 60 to 100 grams of glucose being consumed by the patient, and c) a means for administering intravenously the pulse of insulin at a regular interval of time until the subsequent respiratory quotient shows an improvement over the steady baseline respiratory quotient, the improvement being a respiratory quotient of 0.90 or greater, the subsequent respiratory quotient improvement over the steady baseline respiratory quotient being a measurement of sufficient insulin pulses to achieve a stabilization or decrease in 24-hour urinary protein excretion or a stabilization or increase in creatinine clearance.

2. The system of claim 1, wherein the intravenous site further comprises a needle or catheter located in the patient's body, hand or forearm.

3. The system of claim 1, wherein the means for administering the pulse of insulin is an intravenous infusion device.

4. The system of claim 1, wherein the intravenous site is converted to a heparin or a saline lock when the administration of insulin pulses has temporarily ceased between treatments.

* * * * *